United States Patent [19]

Lee

[11] 4,152,334

[45] May 1, 1979

[54] PROCESS FOR PREPARING 5,6-DIHYDRO-2-METHYL-1,4-OXATHIIN DERIVATIVES

[76] Inventor: Wha S. Lee, c/o 678 Portage St., Ottawa, Canada, K1G 1T4

[21] Appl. No.: 838,679

[22] Filed: Oct. 3, 1977

[30] Foreign Application Priority Data

Apr. 8, 1977 [KR] Rep. of Korea ............................. 841

[51] Int. Cl.$^2$ .......................................... C07D 327/04
[52] U.S. Cl. ................................ 260/327 M; 424/276; 260/327 P
[58] Field of Search ...................... 260/327 M, 327 P; 424/276

[56] References Cited

U.S. PATENT DOCUMENTS

| 3,249,499 | 5/1966 | Schmeling et al. | 424/276 |
| 3,882,237 | 5/1975 | Knight et al. | 424/276 |

OTHER PUBLICATIONS

Breslow et al., Multi-Sulfur and Sulfur And Oxygen Five- And Six- Membered Heterocycles, Part One, pp. 234 to 237 and 241, Interscience Publishers, NY (1966).

Breslow et al., Multi-Sulfur and Sulfur And Oxygen Five- And Six- Membered Heterocycles, Part Two, pp. 842 to 844, Interscience Publishers (NY), 1966.

Djerassi et al., J. Am. Chem. Soc., vol. 75, pp 3704–3708 (1953).

Schmidt et al., Chemiches Berichte, vol. 97, pp. 1649 to 1653 (1964).

Emerson et al., Chem. Abstracts, vol. 75, abst. 129470f (1971) (abst. of Tetrahedron Lett., 1971, pp. 3445–3448).

*Primary Examiner*—John D. Randolph
*Attorney, Agent, or Firm*—Johnson & Hicks

[57] ABSTRACT

5,6-Dihydro-2-methyl-1,4-oxathiin derivatives are prepared by converting an appropriate 1,3-oxathiolane derivative to its sulfoxide and subjecting the sulfoxide to acid catalyzed rearrangement to form the desired product.

6 Claims, No Drawings

PROCESS FOR PREPARING 5,6-DIHYDRO-2-METHYL-1,4-OXATHIIN DERIVATIVES

This invention relates to a new and improved method of preparing 5,6-dihydro-2-methyl-1,4-oxathiin derivatives (I) represented by the formula

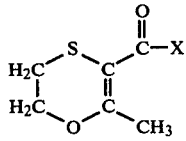

wherein X is an amino or alkoxy group. The amino group may be primary, secondary or tertiary, and the alkyl moiety of the alkoxy group may be primary, secondary or tertiary. It is apparent that the derivatives I may represent 5,6-dihydro-2-methyl-1,4-oxathiin-3-carboxamides (Ia) when X is the amino group, and 5,6-dihydro-2-methyl-1,4-oxathiin-3-carboalkoxides (Ib) when X is the alkoxy group.

The compounds Ia and Ib are known chemicals having been described in U.S. Pats. Nos. 3,249,499 (May 3, 1966), 3,393,202 (July 16, 1968), and in Can. Pats. Nos. 787,893 (June 18, 1968), 791,151 (July 30, 1968). 5,6-Dihydro-2-methyl-1,4-oxathiin-3-carboxamides (Ia) have been described as having fungicidal and bactericidal properties. The compounds Ib are also useful chemicals as these can be converted to compounds Ia.

The prior art preparation of 5,6-dihydro-2-methyl-1,4-oxathiin-3-carboxamides (Ia) has been effected by two methods. The first method has included (1) converting acetoacetamide to alphachloroacetoacetamide, (2) reacting this with 2-mercaptoethanol in a mutual solvent in the presence of a base, (3) subjecting the resulting product to acidic conditions whereby it cyclizes with loss of water to form 5,6-dihydro-2-methyl-1,4-oxathiin-3-carboxamide (Ia) and (4) isolating said product from the reaction mixture. The second method of preparing same has used alkyl acetoacetate in place of acetoacetamide as a starting material. Thus, from the procedure analogous to the first method described above, the resulting 5,6-dihydro-2-methyl-1,4-oxathiin-3-carboalkoxide (Ib) was converted to 5,6-dihydro-2-methyl-1,4-oxathiin-3-carboxamide (Ia).

Prior art process as generally outlined is subject to certain disadvantage. One disadvantage of the prior art process is that the first method described above is sensitive to side reaction and the yields of 5,6-dihydro-2-methyl-1,4-oxathiin-3-carboxamides (Ia) obtained by such method are lower than desired. Another disadvantage is that, in the first and second methods described above, the preparation of alpha-haloacetoacetamide or alkyl alpha-haloacetoacetate is somewhat inconvenient step, and overall yield of 5,6-dihydro-2-methyl-1,4-oxathiin-3-carboxamide (Ia) via the second method is relatively low.

It is an object of the present invention to provide a new and improved method for preparing 5,6-dihydro-2-methyl-1,4-oxathiin derivatives (I).

It is another object of the present invention to provide methods of preparing the sulfoxides of 1,3-oxathiolane derivatives, which can be simply and efficiently converted to 5,6-dihydro-2-methyl-1,4-oxathiin derivatives (I).

SUMMARY OF THE INVENTION

These and other objects of the present invention are achieved in accordance with the present invention which provides a novel process of preparing 5,6-dihydro-2-methyl-1,4-oxathiin derivatives (I) comprising the steps of: (1) reacting acetoacetamide or alkyl acetoacetate with 2-mercaptoethanol (II) in the presence of a acid catalyst to form 1,3-oxathiolane derivative IV, (2) converting IV into corresponding sulfoxide V, and (3) subjecting the sulfoxide to acid catalyzed rearrangement whereby a ring expansion takes place vvia sulfenic acid intermediate VI to form compound I with loss of water.

DETAILED DESCRIPTION OF THE INVENTION

A new process for the preparation of 5,6-dihydro-2-methyl-1,4-oxathiin derivatives (I) has been discovered. The process, represented by the following equations, involves preparing the appropriate 1,3-oxathiolane sulfoxides V, and then subjecting these sulfoxides to a ring expansion reaction.

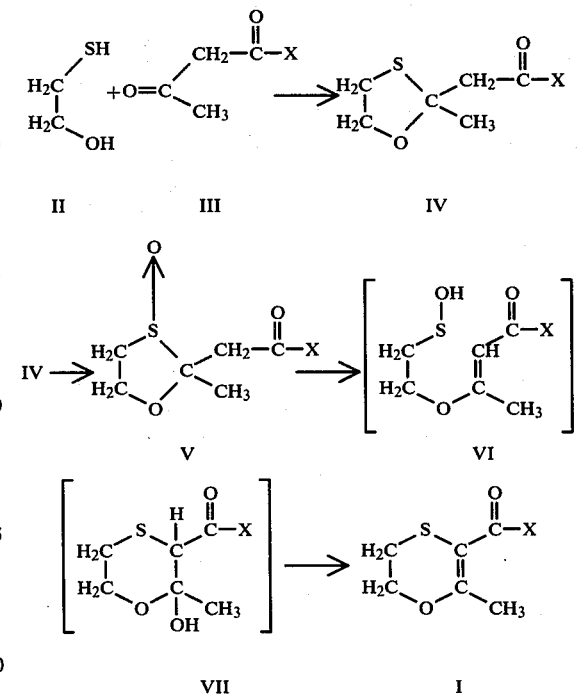

In the above equations X is a primary, secondary or tertiary amino group, or X is an alkoxy group in which the alkyl moiety is primary, secondary or tertiary.

1,3-Oxathiolane derivative IV, which is an ethylene hemithioketal of the carbonyl compound III, can be prepared by reacting acetoacetamide (III, e.g., X=C6H5NH) or alkyl acetoacetate (III, e.g., X=OEt) with 2-mercaptoethanol (II) in the presence of a acid catalyst in a refluxing solvent such as benzene or ether. The sulfoxidation of 1,3-oxathiolane IV may be carried out with organic peracid or hydrogen peroxide in methylene chloride, chloroform or acetic acid at a temperature of 0° to 20° C. It has been found in the present invention that the sulfoxide V thus formed is a mixture of cis and trans isomeric sulfoxides Va and Vb as shown in the formula below.

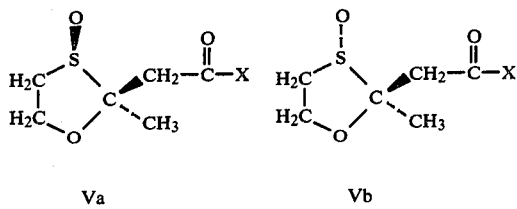

Va                              Vb

In sulfoxide Va, the S→O bond and

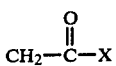

group are cis to each other and in sulfoxide Vb these two groups are trans to each other. These isomeric sulfoxides can be identified from the nuclear magnetic resonance spectroscopic data and other physical and chemical properties of the compounds. If desired, these isomers can be separated by column or preparative thin layer chromatography.

1,3-Oxathiolane sulfoxides V are new compounds, and since they are valuable intermediates in the process of this invention, they also form part of the invention.

It has been also found in the present invention that both the sulfoxides Va and Vb undergo facile rearrangement under very mild conditions to give 5,6-dihydro-2-methyl-1,4-oxathiin derivative I. The ring expansion reaction can be conducted preferably in solution in the presence of a acid catalyst at a temperature of about 25° to 100°. The acid catalysts employed are organic acids such as p-toluenesulfonic acid, methanesulfonic acid, and the suitable solvents are dimethylformide, dimethylacetamide, benzene, chloroform and methylene chloride.

The reaction may proceed through intermediates VI and VII, neither of which need be isolated. The internal alkene-sulfenic acid intermediate VI readily cyclize to VII. The intermediate VII is dehydrated readily to yield the desired product I under slightly acidic conditions. The dehydration is facilitated by heating, and particularly by heating under reflux conditions to drive off the water formed, conveniently as a azeotrope with benzene or like.

The following examples illustrate in more detail the practice of the invention. It will be understood that the invention is not confined to the specific limitations set forth in the following examples but rather, to the scope of the appended claims.

EXAMPLE 1

Preparation of 2-methyl-2-carboxanilidomethyl-1,3-oxathiolane (IV, X=C$_6$H$_5$NH)

A solution of acetoacetanilide (17.72 g., 0.1 mole), 2-mercaptoethanol (7.81 g., 0.1 mole) and p-toluenesulfonic acid monohydrate (0.16 g.) in anhydrous benzene (40 ml.) was refluxed in a round bottomed flask connected to a Dean-Stark water separator for 5 hr. until no more water appeared in the separator. The water collected was 1.8 ml. (theory 1.8 ml.). the benzene solution was cooled, washed with sodium bicarbonate solution and water, dried (MgSO$_4$), and decolorized (charcoal). Solvent was evaporated at 40 under reduced pressure to give gummy residue (24.7 g.). The residue was crystallized from ethyl acetate-petroleum ether to obtain colorless short needles (21.4 g., 90.2%); m.p. 85–87.

EXAMPLE 2

Preparation of 2-methyl-2-carbethoxymethyl-1,3-oxathiolane (IV, X=OEt)

Method A. A solution of ethyl acetoacetate (13.02 g., 0.10 mole) and 2-mercaptoethanol (7.81 g., 0.10 mole) in anhydrous benzene (40 ml.) containing 0.16 g. of p-toluenesulfonic acid monohydrate was refluxed in a round bottomed flask connected to a Dean-Stark water separator for 4 hr. until no more water appeared in the separator. The water collected was 1.8 ml. (theory 1.8 ml.). The benzene solution was cooled, washed with sodium bicarbonate solution and with water, and dried (MgSO$_4$). Solvent was evaporated at room temperature under reduced pressure to obtain colorless oily residue (17.38 g., 91.30%).

Method B. To a stirred and refluxing solution of ethyl acetoacetate (32.54 g., 0.25 mole) and 2-mercaptoethanol (19.53 g., 0.25 mole) in anhydrous ether (200 ml.) was added BF$_3$.Et$_2$O(35.48 g., 0.25 mole) dropwise over 1 hr. The mixture was allowed to reflux for an additional hour. The resulting reaction mixture was cooled, washed with sodium bicarbonate solution and water, and dried (MgSO$_4$). Solvent was evaporated at room temperature under reduced pressure to give colorless oily residue (42.1 g., 88.48%).

EXAMPLE 3

Preparation of 2-methyl-2-carboxanilidomethyl-1,3-oxathiolane-3-oxide (V, X=C$_6$H$_5$NH)

Method A. A solution of 1,3-oxathiolane (IV, X=C$_6$H$_5$NH) (7.12 g., 0.03 mole) in acetic acid (30 ml.) was cooled to 15°–20° in the ice-bath and 35% hydrogen peroxide (6 ml., about 0.06 mole) in water was added dropwise over 30 min. while stirring the mixture. Stirring was continued at the same temperature for 1 hr. 45 min. To the resulting mixture in the same bath was added in portion 6 N. NaOH solution until the mixture reached pH 7. The product was extracted with methylene chloride, and the extract washed with water and dried (Na$_2$SO$_4$). Solvent was evaporated at room temperature under reduced pressure to obtain white foamy solid residue (7.09 g., 93.33%), as a mixture of cis and trans (ca. 70:30) sulfoxides (Va and Vb, X=C$_6$H$_5$NH) as determined by nmr spectra (benzene-d$_6$). These isomeric sulfoxides were separated by preparative thin layer chromatography. Thus 1.0 g. of the above mixture was chromatographed on silicagel (GF 254) plates using chloroform-methanol as developing solvent (flow rate: Va>Vb) to obtain 0.4968 g. of cis isomer (Va), and 0.2368 g. of trans isomer (Vb). Recrystallized from ethyl acetate-petroleum ether: Va, prisms, m.p. 97°–103° dec.; Vb, crystalline powder, m.p. 121°–125° dec. Nmr (Va+Vb) (C$_6$D$_6$): δ1,27 (s, 2.1 H)[a], 1.58 (s, 0.9 H)[b], 2.32 (m, 3H), 2.90 (s, 0.6H), 3.06 (q, 1.4H), 3.37–4.19 (m, 2H), 6.79–7.88 (m, 5H), 9.22 (s, 0.3H), 9.44 (s, 0.7H), a/b=Va/Vb=2.1/0.9=70/30; Va (C$_6$D$_6$): 1.27 (s, 3H), 2.32 (m, 2H), 3.06 (q, 2H), 3.37–4.19 (m, 2H), 6.79–7.88 (m, 5H), 9.44 (s, 1H); Vb (CDCl$_3$): δ1.54 (s, 3H), 2.74–3.54 (m, 2H), 3.01 (s, 2H), 4,34 (q, 2H), 6.96–7.52 (m, 5H), 8.94 (s, 1H) Found for Va: C, 57.0; H, 5.8; N, 5.3, S, 12.4%; for Vb: C, 57.0, H, 5.7, N, 5.4, S, 12.5% $C_{12}H_{15}NS$ requires C, 56.89; H, 5.97; N, 5.53; S, 12.66%

Method B. To a solution of 1,3-oxathiolane (IV, $X=C_6H_5NH$) (8.000 g., 0.0337 mole) in chloroform (200 ml.) cooled in the ice-salt bath at 0°-5° was added dropwise while stirring the mixture, a cool solution of 85% m-chloroperbenzoic acid (6,84 g., 0.0337 mole) in chloroform (200 ml.) over 60 min. Stirring was continued at the same temperature for 3 hr. The resulting reaction mixture was washed with cold saturated sodium bicarbonate solution and water, and dried ($Na_2SO_4$). Solvent was evaporated at room temperature under reduced pressure to give oily residue. This was dissolved in methylene chloride and the solvent evaporated as above to obtain white foamy solid residue (8.5 g., 99.5%), as a mixture of cis and trans (ca. 85:15) isomeric sulfoxides (Va and Vb, $X=C_6H_5NH$) as determined by nmr spectrum (benzene-$d_6$). (See Method A)

EXAMPLE 4

Preparation of
2-methyl-2-carboethoxymethyl-1,3-oxathiolane-3-oxide
(IV, X=OEt)

Method A. To a stirred solution of 1,3-oxathiolane (IV, X=OEt) (3.806 g., 0.02 mole) in acetic acid (20 ml.) at 15°-20° was added 35% hydrogen peroxide (4 ml., about 0.04 mole) in water dropwise over 30 min. Stirring was continued at the same temperature for 2 hr. The resulting reaction mixture was placed in the ice-salt bath at $-3°$ to 3° and diluted with ice-cold chloroform (200 ml.). Keeping the stirred mixture at 3°-8°, 6.25 N. NaOH (about 60 ml.) was added dropwise until it showed pH 7.0. The mixture was shaken and the organic phase separated. The aqueous phase was extracted again with ice-cold chloroform (200 ml.). The combined extract was washed with ice-water and dried ($Na_2SO_4$). Solvent was evaporated at ice-bath temperature under reduced pressure to obtain colorless oily residue (4.076 g., 98.8%), as a mixture of cis and trans (ca. 60:40) isomeric sulfoxides (Va and Vb, X=OEt) as determined by nmr spectrum (benzene-$d_6$): $\delta$0.99 (2t, 3H), 1,32 (s, 1.8H)$^a$, 1,48 (s, 1.2H)$^b$, 2.18-3.03 (m, 4H), 3.40-4.28 (m, 4H), a/b=Va/Vb=1.8/1.2=60/40 Found: C, 46.0: H, 6.7: S, 14.5% $C_8H_{14}SO_4$ requires C, 46.58; H, 6.84, S, 15.55% These sulfoxides, particularly cis isomer, are unstable, and decompose to compound VII (X=OEt) even at room temperature. It is hard to obtain analytically pure sample due to the instablity under the condition of purification. However, these sulfoxides were confirmed by converting to the known compound (See EXAMPLE 6).

Method B. To a stirred solution of 1,3-oxathiolane (IV, X=OEt) (2.000 g., 0.0105 mole) in chloroform (50 ml.) cooled in the ice-bath at 0°-5° was added dropwise a solution of m-chloroperbenzoic acid in chloroform (50 ml.) over 60 min. Stirring was continued at the same temperature for 4 hr. The resulting reaction mixture was washed with ice-cold saturated sodium bicarbonate solution and ice-water, and dried ($Na_2SO_4$). Solvent was evaporated at the ice-bath temperature under reduced pressure to obtain colorless liquid residue (2.07 g., 95.0%), as a mixture of cis and trans (ca. 70:30) isomeric sulfoxides (Va and Vb, X=OEt) as determined by nmr spectrum. (See Method A)

EXAMPLE 5

Preparation of
5,6-dihydro-2-methyl-1,4-oxathiin-3-carboxanilide
(Ia=$C_6H_5NH$)

(A) From a mixture of cis and trans isomeric sulfoxides. A solution of a mixture of cis and trans (ca. 85:15) isomeric sulfoxide (Va and Vb, $X=C_6H_5NH$) (0.5000 g., 0.00197 mole) in 1:1 mixture (20 ml.) of benzene-dimethylformamide containing a catalytic amount of p-toluenesulfonic acid monohydrate was placed in the water-bath at 50° and allowed to stir for 26 hr. Solvent was evaporated at 25°-50° to give oily residue (0.5538). This residue was redissolved in benzene (20 ml.) and the solution refluxed with Dean-Stark water trap for 7 hr. The resulting reaction mixture was washed with sodium bicarbonate solution and with water, and dried ($Na_2SO_4$). Benzene was evaporated at 40° under reduced pressure to obtain crystalline solid residue (0.4455 g., 96.05%), Ia ($X=C_6H_5NH$) as shown by nmr spectrum. Recrystallization from ethyl acetate-petroleum ether gave colorless needles (0.3942 g., 85.0%), m.p. 90°-91°. Nmr ($CDCl_3$): $\delta$2.24 (s, 3H), 2.92 (t, 2H), 4.34 (t, 2H), 6,96-7.54 (m, 5H), 7.94 (s, 1H). This product is identical in every respect to that prepared by the previously known method [U.S. Pat. No. 3,393,202 (July 16, 1968)] [Note]: In the above patent compound Ia ($X=C_6H_5NH$) was alternatively named 2,3-dihydro-5-carboxanilido-6-methyl-1,4-oxathiin.

(B) From cis sulfoxide
A solution of cis sulfoxide (Va, $X=C_6H_5NH$) (0.250 g., 0.000987 mole) in 1:1 mixture (10 ml.) of benzene-dimethylformamide containing catalytic amount of p-toluenesulfonic acid monohydrate was placed in the water-bath at 50° and allowed to stir for 21 hr. Solvent was evaporated at 25°-50° to give oily residue (0.5538 g.). This residue was redissolved in benzene (20 ml.) and the solution was refluxed with Dean-Stark water trap for 4 hr. The resulting reaction mixture was washed with water and dried ($Na_2SO_4$). Benzene was evaporated at 40° under reduced pressure to obtain crystalline solid residue (0.2144 g., 92.45%), Ia (X—$C_6H_5NH$). This product is identical to that obtained from the preceding reaction (A).

(C) From trans sulfoxide
A solution of trans sulfoxide (Vb, $X=C_6H_5NH$) (0.1124 g., 0.0004436 mole) in 1:1 mixture (5 ml.) of benzene-dimethylformamide containing catalytic amount of p-toluenesulfonic acid monohydrate was placed in the water-bath at 50° and allowed to stir for 48 hr. Solvent was evaporated at 25°-50° to give oily residue (0.118 g.). This residue was redissolved in benzene (20 ml.) and the solution refluxed with Dean-Stark water trap for 5 hr. Solvent was evaporated at 40° under reduced pressure to obtain solid residue (0.0974 g., 93.42%), Ia ($X=C_6H_5NH$). This product is identical to that obtained from the preceding reaction (B).

EXAMPLE 6

Preparation of
5,6-dihydro-2-methyl-1,4-oxathiin-3-carboethoxide (Ib, X=OEt)

A solution of a mixture of cis and trans (ca. 70:30) isomeric sulfoxides (Va and Vb, X=OEt) (0.500 g., 0.00242 mole) in 1:1 mixture (20 ml.) of benzene-dimethylformamide containing catalytic amount of p-toluenesulfonic acid monohydrate was placed in the water-bath at 50° and allowed to stir for 6 hr. Solvent was evaporated at 25°–50° under reduced pressure to give oily liquid residue (0.4342 g.). The residue was dissolved in benzene (20 ml.) and the solution refluxed with Dean-Stark water trap for 4 hr. The resulting reaction mixture was washed with sodium bicarbonate solution and with water, dried (Na$_2$SO$_4$) and decolorized (charcoal). Benzene was evaporated at 40° under reduced pressure to obtain brown oily liquid residue (0.4106 g., 90.0%), Ib (X=OEt). Nmr (CDCl$_3$): δ1.29 (t, 3H), 2.30 (s, 3H), 2.94 (t, 2H), 4.20 (q, 2H), 4.32 (t, 2H). The product is identical in every respect to that prepared by the previously known method [U.S. Pat. No. 3,393,202 (July 16, 1968)] [Note]: In the above patent the compound Ib (X=OEt) was alternatively named ethyl 2,3-dihtdro-6-methyl-1,4-oxathiin-5-carboxylate.

I claim:

1. The process of preparing 5,6-dihydro-2-methyl-1,4-oxathiin derivative of the formula

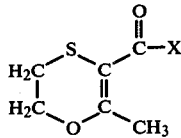

wherein X is an amino group having the formula

wherein R and R' are the same or different and are selected from the group consisting of hydrogen, phenyl, alkyl having up to 15 carbon atoms, cyclohexyl, nitrophenyl, alkoxyphenyl in which the alkoxy group has up to 4 carbon atoms, benzyl, carboxyphenyl, furfuryl, halophenyl, tolyl, naphthyl, biphenyl and hydroxyphenyl; or X is an alkoxy group —OR, in which R is primary, secondary or tertiary alkyl group having up to 6 carbon atoms; comprising subjecting a 1,3-oxathiolane sulfoxide of the formula

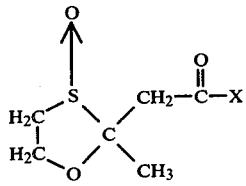

wherein X is the same as in the formula I, in a solvent to slightly acidic conditions whereby ring expansion takes place via sulfenic acid intermediate to form compound I with loss of water, and subsequently isolating this from the resulting mixture.

2. The process of claim 1 preparing the 1,3-oxathiolane sulfoxide V comprising reacting a 1,3-oxathiolane of the formula

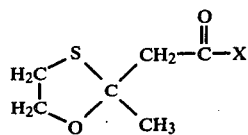

wherein X is the same as in the formula V, with organic peracid, hydrogen peroxide or other oxidizing agent in a solvent to form sulfoxide V, and subsequently isolating said sulfoxide V from the resulting mixture.

3. The method of claim 2 including separating cis and trans sulfoxides Va and Vb, respectively, of the formula

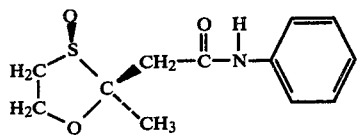

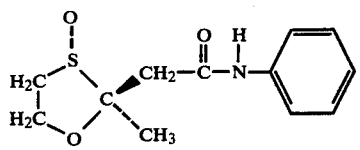

from their isomeric mixture prepared from 1,3-oxathiolane IV (X=C$_6$H$_5$NH) according to the process in claim 2, by thin layer or column chromatography using silica gel and chloroform-methanol or the like as a developing solvent.

4. A 1,3-oxathiolane sulfoxide of the formula

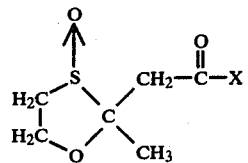

wherein X is an amino group having the formula,

wherein R and R' are the same or different and are selected from the group consisting of hydrogen, phenyl, alkyl having up to 15 carbon atoms, cyclohexyl, nitrophenyl, alkoxyphenyl in which the alkoxy group has up to 4 carbon atoms, benzyl, carboxyphenyl, furfuryl, halophenyl, tolyl, naphthyl, biphenyl and hydroxyphenyl; or X is an alkoxy group —OR, in which R is primary, secondary or tertiary alkyl group having up to 6 carbon atoms.

5. A compound selected from the group comprising 2-methyl-2-carboxanilidomethyl-1,3-oxathiolane-3-oxide, the cis and trans sulfoxide isomers thereof and mixtures thereof.

6. 2-Methyl-2-carboethoxymethyl-1,3-oxathiolane-3-oxide.

* * * * *